Figure 1:
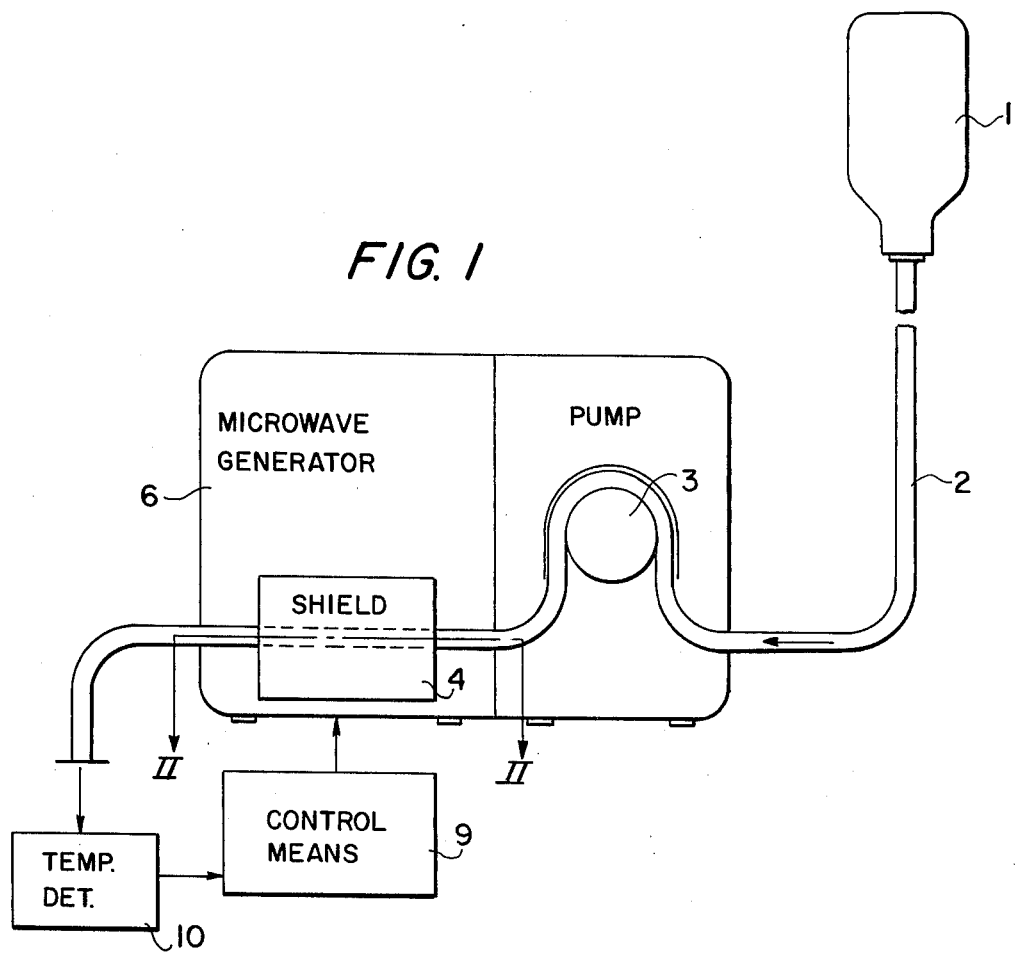

United States Patent [19]
Camph et al.

[11] 3,963,892
[45] June 15, 1976

[54] CONTROLLING THE MICROWAVE HEATING OF FLOWING BLOOD AS A FUNCTION OF HEATED BLOOD TEMPERATURE

[75] Inventors: Sven Erik Camph, Hollviksnas; Kjell Ake Bertil Holmgren, Trelleborg, both of Sweden

[73] Assignee: Camph Engineering Company AB, Malmo, Sweden

[22] Filed: June 13, 1973

[21] Appl. No.: 369,437

[30] Foreign Application Priority Data
June 14, 1972 United Kingdom............... 27759/72

[52] U.S. Cl.................. 219/10.55 M; 219/10.55 A
[51] Int. Cl.²........................................... H05B 9/06
[58] Field of Search................ 219/10.55, 10.55 A, 219/10.55 R, 10.55 M; 128/214 A, 399;

[56] References Cited
UNITED STATES PATENTS

| | | | |
|---|---|---|---|
| 2,585,970 | 2/1952 | Shaw............................ | 219/10.55 R |
| 2,833,657 | 5/1958 | Copsan........................ | 219/10.55 R |
| 3,092,514 | 6/1963 | Tomberlin.................... | 219/10.55 R |
| 3,427,422 | 2/1969 | Muller.......................... | 219/10.55 |
| 3,462,575 | 8/1969 | Holaday....................... | 219/10.55 |
| 3,495,648 | 2/1970 | Amadon...................... | 219/10.55 UX |
| 3,668,358 | 6/1972 | Steustrom.................... | 219/10.55 A |
| 3,778,578 | 12/1973 | Long............................ | 219/10.55 R |

*Primary Examiner*—Bruce A. Reynolds
*Attorney, Agent, or Firm*—Laurence R. Brown

[57] ABSTRACT

Blood is heated by microwaves confined inside a chamber into which the blood is passed.

1 Claim, 2 Drawing Figures

CONTROLLING THE MICROWAVE HEATING OF FLOWING BLOOD AS A FUNCTION OF HEATED BLOOD TEMPERATURE

This invention relates to a method of heating blood (which may be whole blood or plasma) and to an apparatus for effecting the said method.

Blood is normally stored at a low temperature, and prior to introducing it into a patient in large amounts it must be preheated to a desired temperature within narrow limits. The pre-heating should be effected quickly, but in order to avoid damage to the blood, the temperature gradients should be low and local overheating should be avoided. In the event of stopping the flow of blood to be heated any overheating caused only by the heat capacity of the heating device should be avoided.

A well-known but somewhat unsatisfactory method of heating blood is to use a heat exchanger in which the heating medium is warm water. It has therefore been proposed to store the blood in containers of flexible plastic material and mount said containers directly in contact with two electrodes between which an oscillating or alternating electromagnetic field is developed. However, it has been impossible to avoid local overheating or burning in various parts of the container and the heated blood has been unsafe for transfusion.

The present invention is therefore intended to provide an improved method and apparatus for heating blood by exposing it to a high-frequency electric field whilst avoiding or reducing any risk of local overheating.

According to the invention there is employed a method of heating blood, characterised by the steps of introducing the blood into a shield chamber, exposing the blood to the heating action of microwaves by means of electrodes inside the chamber and emitting microwaves generated by a generator located outside the chamber, and controlling the duration of exposure and energy of the microwaves so that the blood is heated to the desired temperature.

It is advantageous to pass the blood through a hose leading through the chamber, and preferably the generator is controlled by control means responsive to the temperature of the blood which has passed through the chamber.

For effecting this method according to the invention there is provided an apparatus for heating blood, comprising a shield chamber, a high-frequency microwave generator, electrodes within the chamber and emitting microwaves generated by the said generator, and means for enclosing blood to be exposed to the heating action of the microwaves within the chamber.

Figure 2:
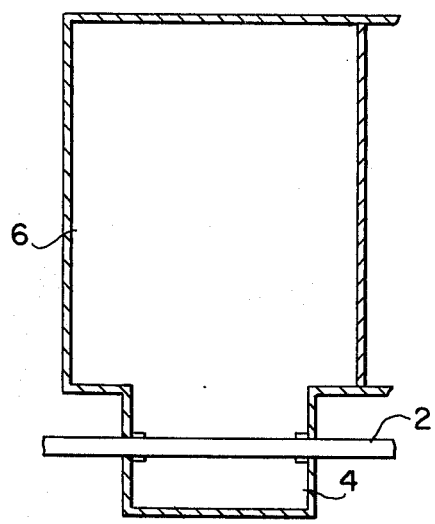

How the invention may be put into practice is described with reference to the accompanying drawings in which FIG. 1 schematically shows a side view of an apparatus according to the invention, and FIG. 2 is a view in section along the line II—II of FIG. 1.

Referring first to FIGS. 1 and 2, a container 1 for blood at low temperature is connected to a flexible hose 2 passing a pumping device 3 and entering a shield chamber 4 in which the hose 2 as well as its contents is exposed to the heating effect of microwaves emitted by a generator 6 located adjacent to chamber 4. The heated blood may be used directly after leaving the device described.

Control means 9 responsive to the temperature of the blood leaving chamber 4 is used for controlling the generator 6 by means of a temperature responsive device 10.

It will be understood that in case of stopping the flow of blood, the heating will immediately cease and that there is no heat capacity in the heating device. Also the apparatus may be used continuously by using more containers like the container 1, and the apparatus needs no sterilization during intervals between use providing that the hose is sterile or is replaced by a fresh sterile hose when necessary.

We claim:

1. A method of heating blood for on line use directly into a patient, characterized by the steps of introducing a continuous flow of blood into a shield chamber through a microwave preamble flexible hose to pass therethrough, exposing the blood flowing within said chamber to the heating action of microwaves, and controlling the duration of exposure and energy of the microwaves from the microwave generator in response to the temperature of the blood which has passed through said chamber so that the blood is heated to the desired temperature.

* * * * *